(12) United States Patent
Foster (10) Patent No.: US 8,168,204 B2
(45) Date of Patent: May 1, 2012

(54) **PHEP, AN AMINO ACID PERMEASE OF *STAPHYLOCOCCUS AUREUS***

(75) Inventor: Simon J. Foster, Sheffield (GB)

(73) Assignee: Absynth Biologics Ltd., Sheffield (GB)

( * ) Notice: Subject to any disclaimer, the term of this patent is extended or adjusted under 35 U.S.C. 154(b) by 0 days.

(21) Appl. No.: 12/766,187

(22) Filed: Apr. 23, 2010

(65) Prior Publication Data

US 2011/0171237 A1 Jul. 14, 2011

Related U.S. Application Data

(62) Division of application No. 11/587,886, filed as application No. PCT/GB2005/001384 on Apr. 8, 2005, now Pat. No. 7,740,869.

(30) Foreign Application Priority Data

Apr. 29, 2004 (GB) .................................. 0409559.2

(51) Int. Cl.
*A61K 39/085* (2006.01)
(52) U.S. Cl. ............... 424/243.1; 424/185.1; 424/190.1; 424/234.1; 530/300; 530/350
(58) Field of Classification Search ........................ None
See application file for complete search history.

(56) References Cited

U.S. PATENT DOCUMENTS

2003/0054436 A1 3/2003 Kunsch et al.

FOREIGN PATENT DOCUMENTS

WO 02/094868 A2 11/2002

OTHER PUBLICATIONS

Accession No. Q931S5, Dec. 1, 2001.
Accession No. Q99UE3, Jun. 1, 2001.
Horsburgh, Malcolm J. et al., "PheP, a Putative Amino Acid Permease of *Staphylococcus aureus*, Contributes to Survival In Vivo and during Starvation," Infection and Immunity, vol. 72, No. 5, pp. 3073-3076 (May 2004).
Kuroda, Makoto et al., "Whole genome sequencing of meticillin-resistant *Staphylococcus aureus*," The Lancet, vol. 357, pp. 1225-1240 (Apr. 21, 2001).
Holden, Matthew T.G. et al., "Complete genomes of two clinical *Staphylococcus aureus* strains: Evidence for the rapid evolution of virulence and drug resistance," PNAS, vol. 101, No. 26, pp. 9786-9791 (Jun. 29, 2004).
Baba, Tadashi et al., "Genome and virulence determinants of high virulence community-acquired MRSA," The Lancet, vol. 359, pp. 1819-1827 (May 25, 2002).

*Primary Examiner* — Jennifer Graser
(74) *Attorney, Agent, or Firm* — Janet Sleath; Speckman Law Group PLLC (57) ABSTRACT

The present invention relates to antigenic polypeptides expressed by pathogenic microbes, including antigenic polypeptides encoded by the nucleic acid sequence of FIG. 1, vaccines comprising the antigenic polypeptides and therapeutic antibodies directed to the antigenic polypeptides.

8 Claims, 7 Drawing Sheets

Figure 1

(a) LYFWDTFKFFHPIT
    CTTTATTTCTGGGACACATTTAAATTTTTCCACCCCATTACT (b) GHTYGFENYTKGQAPFVG
    GGTCATACATATGGATTTGAAAACTATACAAAAGGCCAAGCACCGTTTGTTGGT (c) PYTDPSLLRASSSISQSPFTI
    CCGTACACAGATCCATCATTATTAAGAGCAAGTAGTTCAATAAGTCAAAGCCCATTTACAATT

Figure 2

ATGGAAGATAATAAAATGAACCGTAGTCTTAACTCAAGACACATTTCCATGATTGCTATA
GGTGGTGCAATTGGGACTGGTCTATTTGTAGCTACTGGTAATATCATTTCTCAAGCTGGT
CCTGGAGGCGCTATACTCGCTTATCTTGTTATTGGTGTCATGCTATATTTCTTAATGTCA
TCAATTGGAGAGTTGGCAACATTTTATCCAGTATCAGGTTCATTCAGCTCTTATTCAACA
CGCTTTATTGACTCATCTCTTGGCTTTACCATGGGATGGTTGTATTGGGCATTGTGGTCA
TTAGTTACAAGTGTTGATGTCATAGTAGCGTCAAATGTGCTTTATTTCTGGGACACATTT
AAATTTTTCCACCCCATTACTTGGAGCTTAATCTTTATTACAATTTTACTATTATTAAAC
ATTTTTTCTGTAAAATCATTTGGAGAAACTGAGTTTTGGTTATCATTGATTAAAGTGTTA
ACAATTATCGTATTCGTTATTTTTGGCTTTTTAATGATTTTCGGTATCTTAGGTGGTCAT
ACATATGGATTTGAAAACTATACAAAAGGCCAAGCACCGTTTGTTGGTGGTATCTCTGGT
TTCTTAGGCGTATTATTAGTCGCCGGATTTTCGGTTGGTGGTACAGAAGTAGTAGCAGTA
ACTGCTGGTGAATCAGATGACCCTAAAAAGTCTATGCCTAAGGCAATTAAACAAGTATTT
TGGCGTATTCTTTTATTCTATGTCTTATCAATTGCAGTAATTGGTGCAATTATTCCGTAC
ACAGATCCATCATTATTAAGAGCAAGTAGTTCAATAAGTCAAAGCCCATTTACAATTGTA
TTCGATAGAGTAGGCATAGCCTTTGCAGCATCAGTAATCAACGCGGTTATTTTAACTTCA
TTATTATCCGCTGCAAATTCAGGTGTTTATACAACAGGCAGAATGTTGTATTCCTTAAGT
TCAGACAAAAAAGCACCCCAATTTTTAAGTAAATTAAACAAGACAACTAAGTTACCTTTA
AGAGCATTATTAACTACTTATGCAGTCGTTGTTATTGTTATTATTTATGCAAACTTTAAT
TCAAATGCCGTTTTTAATTTACTTGAAATTATTGGTTCAATGATTATAGTTGTTTGGGGA
TCAAGCATTTGGTCACAAATACGATTGCGACAAGCTATTAAAAAACAAGGTCAAGACCCT
AATAAGGTCCTACCATATAAAGCACCTTTTTATCCATTAGGACCAATCATTGTCATCACT
ACACTATTATTCTTGCTATTTGGTGGCTCAGTTGAATATATTTTAAAAGATCAATGGTTA
AATGCTTTTAAAAACTTTTTACCTTTAATCATTCTAGCGTTGATTTACTTTATTCATAAA
ATCATTCACAAAACAAAATTTGTAAAGCTAGAAACAATTAATTTAAAACCACACGATTAT
GACAATCAAAAATAA

Figure 3

MEDNKMNRSLNSRHISMIAIGGAIGTGLFVATGNIISQAGPGGAILAYLVIGVMLYFLMS
SIGELATFYPVSGSFSSYSTRFIDSSLGFTMGWLYWALWSLVTSVDVIVASNVLYFWDTF
KFFHPITWSLIFITILLLLNIFSVKSFGETEFWLSLIKVLTIIVFVIFGFLMIFGILGGH
TYGFENYTKGQAPFVGGISGFLGVLLVAGFSVGGTEVVAVTAGESDDPKKSMPKAIKQVF
WRILLFYVLSIAVIGAIIPYTDPSLLRASSSISQSPFTIVFDRVGIAFAASVINAVILTS
LLSAANSGVYTTGRMLYSLSSDKKAPQFLSKLNKTTKLPLRALLTTYAVVVIVIIYANFN
SNAVFNLLEIIGSMIIVVWGSSIWSQIRLRQAIKKQGQDPNKVLPYKAPFYPLGPIIVIT
TLLFLLFGGSVEYILKDQWLNAFKNFLPLIILALIYFIHKIIHKTKFVKLETINLKPHDY
DNQK

SEQUENCE LISTING

```
<160> NUMBER OF SEQ ID NOS: 16

<210> SEQ ID NO 1
<211> LENGTH: 31
<212> TYPE: DNA
<213> ORGANISM: Artificial
<220> FEATURE:
<223> OTHER INFORMATION: primer

<400> SEQUENCE: 1
ccagaattct gccaatgatt aactctaatc g                              31

<210> SEQ ID NO 2
<211> LENGTH: 34
<212> TYPE: DNA
<213> ORGANISM: Artificial sequence
<220> FEATURE:
<223> OTHER INFORMATION: primer

<400> SEQUENCE: 2
atgatggtac cagtagctac aaatagacca gtcc                           34

<210> SEQ ID NO 3
<211> LENGTH: 34
<212> TYPE: DNA
<213> ORGANISM: Artificial sequence
<220> FEATURE:
<223> OTHER INFORMATION: primer
```

<400> SEQUENCE: 3
agaggatccg catgtcgcaa tcgtatttgt gacc                                34

<210> SEQ ID NO 4
<211> LENGTH: 34
<212> TYPE: DNA
<213> ORGANISM: Artificial sequence
<220> FEATURE:
<223> OTHER INFORMATION: primer

<400> SEQUENCE: 4
ggactggtct atttctagct actggtacca tcat                                34

<210> SEQ ID NO 5
<211> LENGTH: 32
<212> TYPE: DNA
<213> ORGANISM: Artificial sequence
<220> FEATURE:
<223> OTHER INFORMATION: primer

<400> SEQUENCE: 5
ccggtacccg gattttatga ccgatgatga ag                                  32

<210> SEQ ID NO 6
<211> LENGTH: 32
<212> TYPE: DNA
<213> ORGANISM: Artificial sequence
<220> FEATURE:
<223> OTHER INFORMATION: primer

<400> SEQUENCE: 6
ccggtacctt agaaatccct ttgagaatgt tt                                  32

<210> SEQ ID NO 7
<211> LENGTH: 31
<212> TYPE: DNA
<213> ORGANISM: Artificial sequence
<220> FEATURE:
<223> OTHER INFORMATION: primer

<400> SEQUENCE: 7
gagaggatcc tagatgggag actaaatatg g                                   31

<210> SEQ ID NO 8
<211> LENGTH: 31
<212> TYPE: DNA
<213> ORGANISM: Artificial sequence
<220> FEATURE:
<223> OTHER INFORMATION: primer

<400> SEQUENCE: 8
cacagaattc gaatggtaac atggtaataa t                                   31

<210> SEQ ID NO 9
<211> LENGTH: 42
<212> TYPE: DNA
<213> ORGANISM: Staphylococcus aureus

<400> SEQUENCE: 9
ctttatttct gggacacatt taaatttttc cacccatta ct                        42

<210> SEQ ID NO 10
<211> LENGTH: 14
<212> TYPE: PRT
<213> ORGANISM: Staphylococcus aureus -continued

<400> SEQUENCE: 10

Leu Tyr Phe Trp Asp Thr Phe Lys Phe Phe His Pro Ile Thr
1               5                   10

<210> SEQ ID NO 11
<211> LENGTH: 54
<212> TYPE: DNA
<213> ORGANISM: Staphylococcus aureus

<400> SEQUENCE: 11

```
ggtcatacat atggatttga aaactataca aaaggccaag caccgtttgt tggt         54
```

<210> SEQ ID NO 12
<211> LENGTH: 18
<212> TYPE: PRT
<213> ORGANISM: Staphylococcus aureus

<400> SEQUENCE: 12

Gly His Thr Tyr Gly Phe Glu Asn Tyr Thr Lys Gly Gln Ala Pro Phe
1               5                   10                  15

Val Gly

<210> SEQ ID NO 13
<211> LENGTH: 63
<212> TYPE: DNA
<213> ORGANISM: Staphylococcus aureus

<400> SEQUENCE: 13

```
ccgtacacag atccatcatt attaagagca agtagttcaa taagtcaaag cccatttaca    60
att                                                                  63
```

<210> SEQ ID NO 14
<211> LENGTH: 21
<212> TYPE: PRT
<213> ORGANISM: Staphylococcus aureus

<400> SEQUENCE: 14

Pro Tyr Thr Asp Pro Ser Leu Leu Arg Ala Ser Ser Ser Ile Ser Gln
1               5                   10                  15

Ser Pro Phe Thr Ile
            20

<210> SEQ ID NO 15
<211> LENGTH: 1455
<212> TYPE: DNA
<213> ORGANISM: Staphylococcus aureus

<400> SEQUENCE: 15

```
atggaagata taaaaatgaa ccgtagtctt aactcaagac acatttccat gattgctata    60
ggtggtgcaa ttgggactgg tctatttgta gctactggta atatcatttc tcaagctggt   120
cctggaggcg ctatactcgc ttatcttgtt attggtgtca tgctatattt cttaatgtca   180
tcaattggag agttggcaac attttatcca gtatcaggtt cattcagctc ttattcaaca   240
cgctttattg actcatctct tggctttacc atgggatggt tgtattgggc attgtggtca   300
ttagttacaa gtgttgatgt catagtagcg tcaaatgtgc tttatttctg gacacatttt   360 aaattttcc accccattac ttggagctta atctttatta caatttttact attattaaac   420 attttttctg taaaatcatt tggagaaact gagttttggt tatcattgat taaagtgtta   480
acaattatcg tattcgttat ttttggcttt ttaatgattt tcggtatctt aggtggtcat   540
```

```
acatatggat tgaaaactaa tacaaaaggc caagcaccgt tgttggtgg tatctctggt      600
ttcttaggcg tattattagt cgccggattt tcggttggtg gtacagaagt agtagcagta      660
actgctggtg aatcagatga ccctaaaaag tctatgccta aggcaattaa acaagtattt      720
tggcgtattc ttttattcta tgtcttatca attgcagtaa ttggtgcaat tattccgtac      780
acagatccat cattattaag agcaagtagt tcaataagtc aaagcccatt tacaattgta      840
ttcgatagag taggcatagc ctttgcagca tcagtaatca acgcggttat tttaacttca      900
ttattatccg ctgcaaattc aggtgtttat acaacaggca gaatgttgta ttccttaagt      960
tcagacaaaa aagcaccccca atttttaagt aaattaaaca agacaactaa gttacccttta   1020
agagcattat taactactta tgcagtcgtt gttattgtta ttatttatgc aaactttaat     1080
tcaaatgccg ttttaatttt acttgaaatt attggttcaa tgattatagt tgtttgggga     1140
tcaagcattt ggtcacaaat acgattgcga caagctatta aaaacaaggg tcaagaccct    1200
aataaggtcc taccatataa agcacctttt tatccattag gaccaatcat tgtcatcact    1260
acactattat tcttgctatt tggtggctca gttgaatata ttttaaaaga tcaatggtta   1320
aatgcttta aaaacttttt acctttaatc attctagcgt tgatttactt tattcataaa    1380
atcattcaca aaacaaaatt tgtaaagcta gaaacaatta atttaaaacc acacgattat  1440
gacaatcaaa aataa                                                      1455
```

<210> SEQ ID NO 16
<211> LENGTH: 484
<212> TYPE: PRT
<213> ORGANISM: Staphylococcus aureus

<400> SEQUENCE: 16

```
Met Glu Asp Asn Lys Met Asn Arg Ser Leu Asn Ser Arg His Ile Ser
1               5                   10                  15

Met Ile Ala Ile Gly Gly Ala Ile Gly Thr Gly Leu Phe Val Ala Thr
            20                  25                  30

Gly Asn Ile Ile Ser Gln Ala Gly Pro Gly Gly Ala Ile Leu Ala Tyr
        35                  40                  45

Leu Val Ile Gly Val Met Leu Tyr Phe Leu Met Ser Ser Ile Gly Glu
    50                  55                  60

Leu Ala Thr Phe Tyr Pro Val Ser Gly Ser Phe Ser Ser Tyr Ser Thr
65                  70                  75                  80

Arg Phe Ile Asp Ser Ser Leu Gly Phe Thr Met Gly Trp Leu Tyr Trp
                85                  90                  95

Ala Leu Trp Ser Leu Val Thr Ser Val Asp Val Ile Ala Ser Asn
            100                 105                 110

Val Leu Tyr Phe Trp Asp Thr Phe Lys Phe His Pro Ile Thr Trp
        115                 120                 125

Ser Leu Ile Phe Ile Thr Ile Leu Leu Leu Asn Ile Phe Ser Val
    130                 135                 140

Lys Ser Phe Gly Glu Thr Glu Phe Trp Leu Ser Leu Ile Lys Val Leu
145                 150                 155                 160

Thr Ile Ile Val Phe Val Ile Phe Gly Phe Leu Met Ile Phe Gly Ile
                165                 170                 175

Leu Gly Gly His Thr Tyr Gly Phe Glu Asn Tyr Thr Lys Gly Gln Ala
            180                 185                 190

Pro Phe Val Gly Gly Ile Ser Gly Phe Leu Gly Val Leu Leu Val Ala
        195                 200                 205
```

-continued

```
Gly Phe Ser Val Gly Gly Thr Glu Val Val Ala Val Thr Ala Gly Glu
            210                 215                 220

Ser Asp Asp Pro Lys Lys Ser Met Pro Lys Ala Ile Lys Gln Val Phe
225                 230                 235                 240

Trp Arg Ile Leu Leu Phe Tyr Val Leu Ser Ile Ala Val Ile Gly Ala
                245                 250                 255

Ile Ile Pro Tyr Thr Asp Pro Ser Leu Leu Arg Ala Ser Ser Ser Ile
            260                 265                 270

Ser Gln Ser Pro Phe Thr Ile Val Phe Asp Arg Val Gly Ile Ala Phe
        275                 280                 285

Ala Ala Ser Val Ile Asn Ala Val Ile Leu Thr Ser Leu Leu Ser Ala
    290                 295                 300

Ala Asn Ser Gly Val Tyr Thr Thr Gly Arg Met Leu Tyr Ser Leu Ser
305                 310                 315                 320

Ser Asp Lys Lys Ala Pro Gln Phe Leu Ser Lys Leu Asn Lys Thr Thr
            325                 330                 335

Lys Leu Pro Leu Arg Ala Leu Leu Thr Thr Tyr Ala Val Val Val Ile
            340                 345                 350

Val Ile Ile Tyr Ala Asn Phe Asn Ser Asn Ala Val Phe Asn Leu Leu
        355                 360                 365

Glu Ile Ile Gly Ser Met Ile Ile Val Val Trp Gly Ser Ser Ile Trp
        370                 375                 380

Ser Gln Ile Arg Leu Arg Gln Ala Ile Lys Lys Gln Gly Gln Asp Pro
385                 390                 395                 400

Asn Lys Val Leu Pro Tyr Lys Ala Pro Phe Tyr Pro Leu Gly Pro Ile
                405                 410                 415

Ile Val Ile Thr Thr Leu Leu Phe Leu Leu Phe Gly Gly Ser Val Glu
            420                 425                 430

Tyr Ile Leu Lys Asp Gln Trp Leu Asn Ala Phe Lys Asn Phe Leu Pro
            435                 440                 445

Leu Ile Ile Leu Ala Leu Ile Tyr Phe Ile His Lys Ile Ile His Lys
        450                 455                 460

Thr Lys Phe Val Lys Leu Glu Thr Ile Asn Leu Lys Pro His Asp Tyr
465                 470                 475                 480

Asp Asn Gln Lys
```

PHEP, AN AMINO ACID PERMEASE OF STAPHYLOCOCCUS AUREUS

REFERENCE TO RELATED APPLICATIONS

This application is a divisional of U.S. patent application Ser. No. 11/587,886, filed Aug. 8, 2007, which is the US national stage of PCT/GB2005/001384, filed Apr. 8, 2005, which claims the benefit of Great Britain patent application no. 0409559.2 filed Apr. 29, 2004.

FIELD OF THE INVENTION

The invention relates to antigenic polypeptides expressed by pathogenic microbes, vaccines comprising the antigenic polypeptides and therapeutic antibodies directed to the antigenic polypeptides.

BACKGROUND

Microbial organisms cause a number of fatal or debilitating diseases which affect many millions of people around the world. Current methods to control microbial organisms include the use of antimicrobial agents (antibiotics) and disinfectants. These have proved to be problematic since exposure to these agents places a significant selection pressure resulting in the creation of resistant microbes which can avoid the effects of the antimicrobial agent(s). For example, it has been discovered that microbial organisms have become resistant to triclosan, an agent added to many disinfectants used in households and industrial environments.

An arguably greater problem is the evolution of antibiotic resistant strains of a number of significant pathogenic microbes.

An example of a pathogenic organism which has developed resistance to antibiotics is *Staphylococcus aureus*. *S. aureus* is a bacterium whose normal habitat is the epithelial lining of the nose in about 20-40% of normal healthy people and is also commonly found on people's skin usually without causing harm. However, in certain circumstances, particularly when skin is damaged, this germ can cause infection. This is a particular problem in hospitals where patients may have surgical procedures and/or be taking immunosuppressive drugs. These patients are much more vulnerable to infection with *S. aureus* because of the treatment they have received. Resistant strains of *S. aureus* have arisen in recent years. Methicillin resistant strains are prevalent and many of these resistant strains are also resistant to several other antibiotics. Currently there is no effective vaccination procedure for *S. aureus*. In the US, *S. aureus* infections are the cause of 13% of the two million hospitalised infections each year. This represents 260,000 people with an infection of *S. aureus*, of which 60-80,000 die.

*S. aureus* is therefore a major human pathogen capable of causing a wide range of life threatening diseases including septicaemia, endocarditis, arthritis and toxic shock. This ability is determined by the versatility of the organism and its arsenal of components involved in virulence. Pathogenicity is multifactorial and no one component has shown to be responsible for a particular infection, see Projan, S. J. & Novick, R. P. (1997) in The Staphylococci in Human Disease (Crossley, K. B. & Archer, G. L., eds.) pp. 55-81.

At the onset of infection, and as it progresses, the needs and environment of the organism changes and this is mirrored by a corresponding alteration in the virulence determinants which *S. aureus* produces. At the beginning of infection it is important for the pathogen to adhere to host tissues and so a large repertoire of cell surface associated attachment proteins are made. These include collagen-, fibrinogen- and fibronectin-binding proteins. The pathogen also has the ability to evade host defences by the production of factors that reduce phagocytosis or interfere with the ability of the cells to be recognised by circulating antibodies.

Often a focus of infection develops as an abscess and the number of organisms increases. *S. aureus* has the ability to monitor its own cell density by the production of a quorum sensing peptide. Accumulation of the peptide, associated with physiological changes brought about by the beginning of starvation of the cells, elicits a switch in virulence determinant production from adhesins to components involved in invasion and tissue penetration. These include a wide range of hemolysins, proteases and other degradative enzymes.

During the process of any infection, the virulence determinants made by *S. aureus* are produced in response to environmental and physiological stimuli. These stimuli will be dependent on the niche within the body and will change as the infection progresses. Little is known of the conditions in vivo and it is likely that some components are produced solely in this environment. These are therefore potential vaccine components, which could not be discovered by previous techniques.

Many vaccines are produced by inactivated or attenuated pathogens which are injected into an individual. The immunised individual responds by producing both a humoral (antibody) and cellular (cytolytic T cells, CTL's) response. For example, hepatitis vaccines are made by heat inactivating the virus and treating it with a cross linking agent such as formaldehyde. An example of an attenuated pathogen useful as a vaccine is represented by polio vaccines which are produced by attenuating a live pathogen.

However the use of attenuated organisms in vaccines for certain diseases is problematic due to the lack of knowledge regarding the pathology of the condition and the nature of the attenuation. For certain viral agents this is a particular problem since viruses, in particular retroviruses, have an error prone replication cycle which results in viable mutations in the genes which comprise the virus. This can result in alterations to antigenic determinants which have previously been used as vaccines.

The development of so-called subunit vaccines (vaccines in which the immunogen is a fragment or subunit of a protein or complex expressed by a particular pathogenic organism) has been the focus of considerable medical research. The need to identify candidate molecules useful in the development of subunit vaccines is apparent not least because conventional chemotherapeutic approaches to the control of pathogenic organisms has more recently been stymied by the development of antibiotic resistance.

SUMMARY

The invention relates to antigenic polypeptides expressed during an infection by a pathogenic microbe and their use in vaccination.

Figure 1:
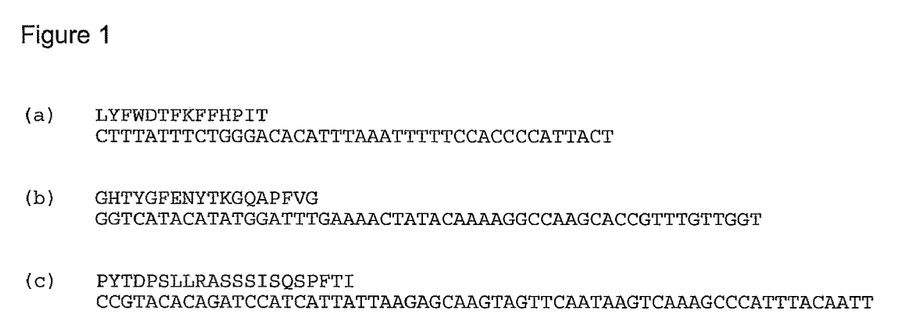
FIG. 1 shows DNA sequences (a, b and c; SEQ ID NO: 9, 11 and 13, respectively), and corresponding amino acid sequences (SEQ ID NO: 10, 12 and 14, respectively), encoding putative extracytoplasmic loops of a *Staphylococcus aureus* PheP.

According to a first aspect of the invention there is provided an antigenic polypeptide, or part thereof, encoded by an isolated nucleic acid sequence selected from the group consisting of:

i) a nucleic acid sequence as shown in FIG. 1 (SEQ ID NO: 9, 11 and 13);
ii) a nucleic acid sequence as in (i) which encodes a polypeptide expressed by a pathogenic organism;
iii) a nucleic acid sequence which hybridises to the sequence identified in (i) or (ii) above; and iv) a nucleic acid sequence that is degenerate as a result of the genetic code to the nucleic acid sequence defined in (i), (ii) or (ii)

for use as a medicament.

In a preferred aspect of the invention the medicament is a vaccine.

Figure 2:
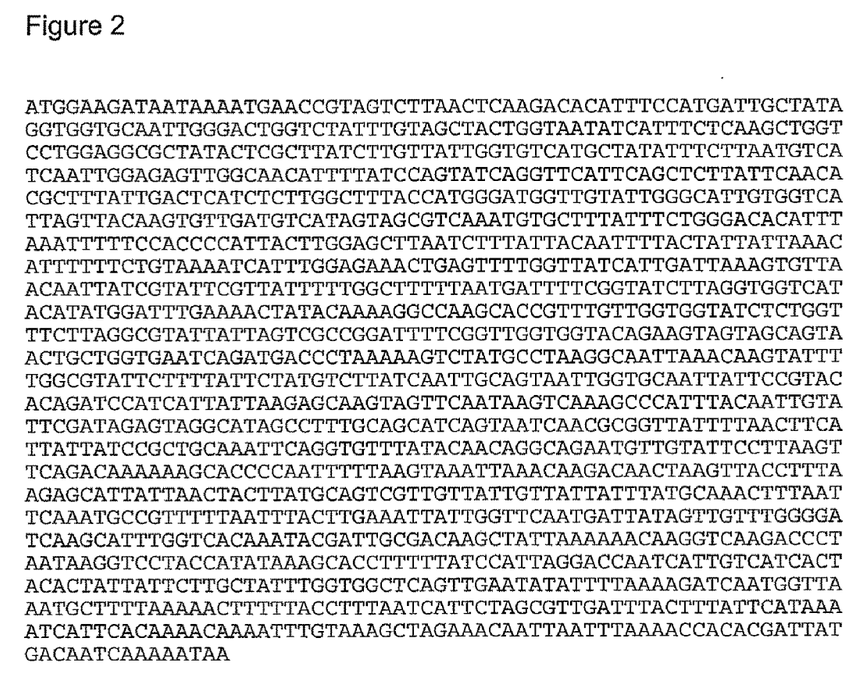
FIG. 2 shows the DNA sequence of a *Staphylococcus aureus* PheP (SEQ ID NO: 15)

In a preferred aspect of the invention, the nucleic acid sequence encoding the antigenic polypeptide of the first aspect of the invention is selected from the group consisting of:

i) a nucleic acid sequence as shown in FIG. 2 (SEQ ID NO: 15);
ii) a nucleic acid sequence as in (i) which encodes a polypeptide expressed by a pathogenic organism;
iii) a nucleic acid sequence which hybridises to the sequence identified in (i) or (ii) above; and
iv) a nucleic acid sequence that is degenerate as a result of the genetic code to the nucleic acid sequence defined in (i), (ii) or (ii)

The nucleic acid encoding the antigenic polypeptide of the first aspect of the invention may anneal under stringent hybridisation conditions to the nucleic acid sequence shown in FIG. 1 (SEQ ID NO: 9, 11 and 13) or FIG. 2 (SEQ ID NO: 15) or to its complementary strand.

Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequences of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m = 81.5° C. + 16.6 \text{ Log } [Na^+] + 0.41[\% G+C] - 0.63(\% \text{ formamide}).$$

The nucleic acid encoding the antigenic polypeptide of the first aspect of the invention may comprise the sequence set out in FIG. 1 (SEQ ID NO: 9, 11 and 13) or 2 (SEQ ID NO: 15) or a sequence which is at least 60%, 65%, 70%, 75%, 80%, 85%, 90%, 95%, for example 98%, or 99%, identical to the nucleic acid sequence set out in FIG. 1 (SEQ ID NO: 9, 11 and 13) or 2 (SEQ ID NO: 15) at the nucleic acid residue level.

"Identity", as known in the art, is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Identity can be readily calculated (*Computational Molecular Biology*, Lesk, A. M. ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., AND Griffin, H. G., eds., Humana Press, New Jersey, 1994; *Sequence Analysis in Molecular Biology*, von Heinje, G., Academic Press, 1987; *and Sequence Analysis Primer*, Gribskov, M. and Devereux, J., eds., M Stockton Press, New York, 1991). While there exist a number of methods to measure identity between two polynucleotide or two polypeptide sequences, the term is well-known to skilled artisans (*Sequence Analysis in Molecular Biology*, von Heinje, G., Academic Press, 1987; *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods commonly employed to determine identity between sequences include, but are not limited to those disclosed in Carillo, H., and Lipman, D., *SIAM J. Applied Math.*, 48: 1073 (1988). Preferred methods to determine identity are designed to give the largest match between the sequences tested. Methods to determine identity are codified in computer programs. Preferred computer program methods to determine identity between two sequences include, but are not limited to, GCG program package (Devereux, J., et al., *Nucleid Acids Research* 12(1): 387 (1984)), BLASTP, BLASTN, and FASTA (Atschul, S. F. et al., *J. Molec. Biol.* 215: 403 (1990)).

The nucleic acid encoding the antigenic polypeptide of the first aspect of the invention may comprise of fragment of a sequence according to the first aspect which is at least 30 bases long, for example, 40, 50, 60, 70, 80 or 90 bases in length.

The nucleic acid sequence encoding the antigenic polypeptide of the first aspect of the invention may be genomic DNA, cDNA or RNA, for example mRNA.

The antigenic polypeptide of the first aspect of the invention may be a cell membrane protein, for example an integral membrane protein.

The antigenic polypeptide of the first aspect of the invention may have permease activity. As used herein "permease" relates to a cell membrane protein that functions as a channel for the transport of a specific molecule in or out of the cell.

Preferably, the antigenic polypeptide of the first aspect of the invention is involved in the transport of one or more amino acids in or out of the cell, for example, the polypeptide may have phenylalanine permease activity.

Preferably, the antigenic polypeptide of the first aspect of the invention is expressed by a pathogenic organism, for example, a bacterium, virus or yeast. Preferably the pathogenic organism is a bacterium.

The bacterium may be selected from the group consisting of:

*Staphylococcus aureus*; *Staphylococcus epidermidis*; *Enterococcus faecalis*; *Mycobacterium tuberculosis*; *Streptococcus* group B; *Streptoccocus pneumoniae*; *Helicobacter pylori*; *Neisseria gonorrhea*; *Streptococcus* group A; *Borrelia burgdorferi*; *Coccidiodes immitis*; *Histoplasma sapsulatum*; *Neisseria meningitidis* type B; *Shigella flexneri*; *Escherichia coli*; *Haemophilus influenzae*.

Preferably the bacterium is of the genus *Staphylococcus* spp. Preferably still the bacterium is *Staphylococcus aureus*.

In a preferred embodiment of the invention, the antigenic polypeptide of the first aspect of the invention is associated with infective pathogenicity of an organism as defined herein.

Figure 3:
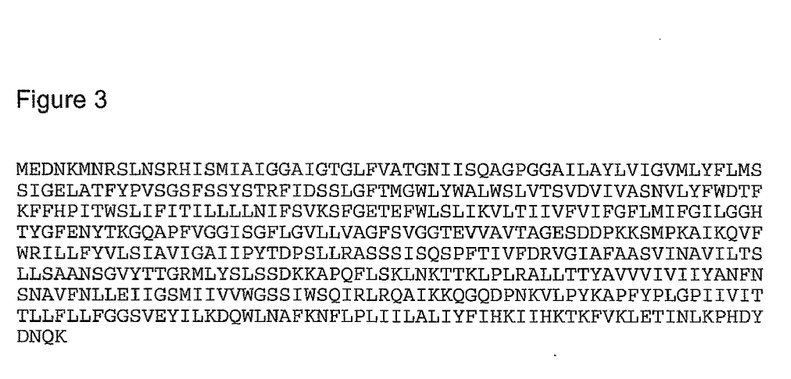
FIG. 3 shows the amino acid sequence (SEQ ID NO: 16) corresponding to the DNA sequence shown in FIG. 2.

In a further preferred aspect of the invention the antigenic polypeptide comprises all, or part of, the amino acid sequence shown in FIG. 1 or 3 (SEQ ID NO: 10, 12, 14 and 16).

As used herein "part" of may include a polypeptide fragment which may be at least 10, 15, 20 or 30 amino acids long.

The antigenic polypeptide of the first aspect of the invention may comprise a non-protein antigen, for example a polysaccharide antigen.

As used herein, the term "polypeptide" means, in general terms, a plurality of amino acid residues joined together by peptide bonds. It is used interchangeably and means the same as peptide, protein, oligopeptide, or oligomer. The term "polypeptide" is also intended to include fragments, analogues and derivatives of a polypeptide wherein the fragment, analogue or derivative retains essentially the same biological activity or function as a reference protein.

According to a second aspect of the invention there is provided a vector comprising a nucleic acid sequence encoding a polypeptide according to the first aspect of the invention.

The vector of the second aspect of the invention may be a plasmid, cosmid or phage. The vector may include a transcription control sequence (promoter sequence) which mediates cell specific expression, for example, a cell specific, inducible or constitutive promoter sequence. The vector may be an expression vector adapted for prokaryotic or eukaryotic gene expression, for example, the vector may include one or more selectable markers and/or autonomous replication sequences which facilitate the maintenance of the vector in either a eukaryotic cell or prokaryotic host (Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994). Vectors which are maintained autonomously are referred to as episomal vectors.

Promoter is an art recognised term and may include enhancer elements which are cis acting nucleic acid sequences often found 5' to the transcription initiation site of a gene (enhancers can also be found 3' to a gene sequence or even located in intronic sequences and is therefore position independent). Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include intermediary metabolites (eg glucose, lipids), environmental effectors (e.g. light, heat,).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

The vector of the second aspect of the invention may include a transcription termination or polyadenylation sequences. This may also include an internal ribosome entry sites (IRES).

The vector may include a nucleic acid sequence that is arranged in a bicistronic or multi-cistronic expression cassette.

According to a third aspect of the invention there is provided a method for the production of a recombinant antigenic polypeptide according to any previous aspect of the invention comprising:
(i) providing a cell transformed/transfected with a vector according to the second aspect of the invention;
(ii) growing said cell in conditions suitable for the production of said polypeptides; and
(iii) purifying said polypeptide from said cell, or its growth environment.

In a preferred aspect of the method of the third aspect, the vector encodes, and thus said recombinant polypeptide is provided with, a secretion signal to facilitate purification of said polypeptide.

According to a fourth aspect of the invention there is provided a cell or cell-line transformed or transfected with the vector according to the second aspect of the invention.

In a preferred embodiment of the invention said cell is a prokaryotic cell, for example, yeast or a bacterium such as *E. coli*. Alternatively said cell is a eukaryotic cell, for example a fungal, insect, amphibian, mammalian, for example, COS, CHO cells, Bowes Melanoma and other suitable human cells, or plant cell.

According to a fifth aspect of the invention there is provided a vaccine comprising at least one antigenic polypeptide, or part thereof, according to the first aspect of the invention. Preferably said vaccine further comprises a carrier and/or adjuvant.

As used herein "part thereof" may include a fragment or subunit of the antigenic polypeptide wherein the fragment or subunit is sufficient to induce an antigenic response in a recipient.

The vaccine according to the fifth aspect may be a subunit vaccine in which the immunogenic part of the vaccine is a fragment or subunit of the antigenic polypeptide according to the first aspect of the invention.

The terms adjuvant and carrier are construed in the following manner. Some polypeptide or peptide antigens contain B-cell epitopes but no T cell epitopes. Immune responses can be greatly enhanced by the inclusion of a T cell epitope in the polypeptide/peptide or by the conjugation of the polypeptide/peptide to an immunogenic carrier protein such as key hole limpet haemocyanin or tetanus toxoid which contain multiple T cell epitopes. The conjugate is taken up by antigen presenting cells, processed and presented by human leukocyte antigens (HLA's) class II molecules. This allows T cell help to be given by T cell's specific for carrier derived epitopes to the B cell which is specific for the original antigenic polypeptide/peptide. This can lead to increase in antibody production, secretion and isotype switching.

An adjuvant is a substance or procedure which augments specific immune responses to antigens by modulating the activity of immune cells. Examples of adjuvants include, by example only, agonsitic antibodies to co-stimulatory molecules, Freunds adjuvant, muramyl dipeptides, liposomes. An adjuvant is therefore an immunomodulator. A carrier is an immunogenic molecule which, when bound to a second molecule augments immune responses to the latter.

In yet a further aspect of the invention there is provided a method to immunise an animal against a pathogenic microbe comprising administering to said animal at least one polypeptide, or part thereof, according to the first aspect of the invention. Preferably, the polypeptide is in the form of a vaccine according to the fifth aspect of the invention. In a preferred method of the invention the animal is human.

Preferably the antigenic polypeptide of the first aspect, or the vaccine of the fifth aspect, of the invention can be delivered by direct injection either intravenously, intramuscularly, subcutaneously. Further still, the vaccine or antigenic polypeptide, may be taken orally. The polypeptide or vaccine may be administered in a pharmaceutically acceptable carrier, such as the various aqueous and lipid media, such as sterile saline, utilized for preparing injectables to be administered intramuscularly and subcutaneously. Conventional suspending and dispersing agents can be employed. Other means of administration, such as implants, for example a sustained low dose releasing bio-observable pellet, will be apparent to the skilled artisan. Preferably the vaccine is against the bacterial species *Staphylococcus aureus*.

It will also be apparent that vaccines or antigenic polypeptides are effective at preventing or alleviating conditions in animals other than humans, for example and not by way of limitation, family pets (e.g. domestic animals such as cats and dogs), livestock (e.g. cattle, sheep, pigs) and horses.

According to a further aspect of the invention there is provided an antibody, or at least an effective binding part thereof, which binds at least one antigenic polypeptide, or part thereof, according to the invention.

In a preferred aspect of the invention said antibody is a polyclonal or monoclonal antibody.

In a further preferred aspect of the invention said antibody is a chimeric antibody produced by recombinant methods to contain the variable region of said antibody with an invariant or constant region of a human antibody.

In a further preferred aspect of the invention, said antibody is humanised by recombinant methods to combine the complimentarity determining regions of said antibody with both the constant (C) regions and the framework regions from the variable (V) regions of a human antibody.

Preferably said antibody is provided with a marker including a conventional label or tag, for example a radioactive and/or fluorescent and/or epitope label or tag.

Preferably said humanised monoclonal antibody to said polypeptide is produced as a fusion polypeptide in an expression vector suitably adapted for transfection or transformation of prokaryotic or eukaryotic cells.

Antibodies, also known as immunoglobulins, are protein molecules which have specificity for foreign molecules (antigens). Immunoglobulins (Ig) are a class of structurally related proteins consisting of two pairs of polypeptide chains, one pair of light (L) (low molecular weight) chain ($\kappa$ or $\lambda$), and one pair of heavy (H) chains ($\gamma$, $\alpha$, $\lambda$, $\delta$ and $\epsilon$), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, $\alpha$, $\lambda$, $\sigma$, $\alpha$, and $\gamma$ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

Chimeric antibodies are recombinant antibodies in which all of the V-regions of a mouse or rat antibody are combined with human antibody C-regions. Humanised antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

In a further preferred embodiment of the invention said antibodies are opsonic antibodies. Opsonins are agents which facilitate the phagocytosis of the above foreign bodies. Phagocytosis is mediated by macrophages and polymorphic leukocytes and involves the ingestion and digestion of microorganisms, damaged or dead cells, cell debris, insoluble particles and activated clotting factors. Opsonic antibodies are therefore antibodies which provide the same function. Examples of opsonins are the Fc portion of an antibody or compliment C3.

In another aspect of the invention there is provided a vector comprising a nucleic acid sequence encoding the humanised or chimeric antibodies according to the invention.

In a yet further aspect of the invention, there is provided a cell or cell line which comprises the vector encoding the humanised or chimeric antibody according to the invention. The cell or cell line may be transformed or transfected with the vector encoding the humanised or chimeric antibody according to the invention.

In a yet further aspect of the invention there is provided a hybridoma cell line which produces a monoclonal antibody as hereinbefore described.

In a further aspect of the invention there is provided a method of producing monoclonal antibodies according to the invention using hybridoma cell lines according to the invention.

In a yet further aspect of the invention there is provided a method for the production of the humanised or chimeric antibody according to the invention comprising:
 (i) providing a cell transformed or transfected with a vector which comprises a nucleic acid molecule encoding the humanised or chimeric antibody according to the invention;
 (ii) growing said cell in conditions suitable for the production of said antibody; and
purifying said antibody from said cell, or its growth environment.

In a further aspect of the invention there is provided a method for preparing a hybridoma cell-line according to the invention comprising the steps of:
 i) immunising an immunocompetent mammal with an immunogen comprising at least one polypeptide having an amino acid sequence as represented in FIG. 1 (SEQ ID NO: 9, 11 and 13) or FIG. 3 (SEQ ID NO: 15), or fragments thereof;
 ii) fusing lymphocytes of the immunised immunocompetent mammal with myeloma cells to form hybridoma cells;
 iii) screening monoclonal antibodies produced by the hybridoma cells of step (ii) for binding activity to the amino acid sequences of (i);
 iv) culturing the hybridoma cells to proliferate and/or to secrete said monoclonal antibody; and
 v) recovering the monoclonal antibody from the culture supernatant.

The immunocompetent mammal may be a mouse, rat or rabbit.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a further aspect of the invention there is provided the use of an antigenic polypeptide according to the first aspect of the invention in the manufacture of a medicament for the treatment or prophylaxis of a *Staphylococcus aureus*-associated disorder.

In a further aspect of the invention there is provided the use of antibodies according to the invention in the manufacture of a medicament for the treatment of *Staphylococcus aureus*-associated disorder.

In a further aspect of the invention there is provided a method of treating a patient comprising administering to the patient an antigenic polypeptide according to the first aspect of the invention, or a vaccine according to the fifth aspect of the invention, or an antibody according to the invention. Preferably the method is for the treatment of a *Staphylococcus aureus*-associated disorder.

A *Staphylococcus aureus*-associated disorder may include, for example, septicaemia; *tuberculosis*; bacteria-associated food poisoning; blood infections; peritonitis; endocarditis; osteomyelitis; sepsis; skin disorders, meningitis; pneumonia; stomach ulcers; gonorrhoea; strep throat; streptococcal-associated toxic shock; necrotizing fasciitis; impetigo; histoplasmosis; Lyme disease; gastro-enteritis; dysentery; shigellosis An embodiment of the invention will now be described by example only and with reference to the following materials, methods and figures:

BRIEF DESCRIPTION OF THE DRAWINGS

FIG. 4. Schematic representation of the pheP-katA locus. The direction of pheP and katA transcription is shown with large arrows and putative transcription terminator structures with ball and stick. (A) 8325-4 (wild-type). (B) Mutant ST1 showing the insertion of Tn917 with the corresponding 380 bp deletion of the 1542 bp coding region of the pheP gene and 1,329 by deletion of the 1419 bp coding region of the katA gene. (C) MJH600 (pheP) showing allelic replacement.

FIG. 5. Pathogenicity of *S. aureus* strains in a murine skin abscess model of infection. Approximately $10^8$ cfu of each strain was inoculated subcutaneously into six to eight-week old BALB/C mice: 8325-4 (wild-type) (n=10), ST1 (pheP katA) (n=10), MJH600 (pheP) (n=10) and PC1839 (sarA) (n=10). Seven days after infection mice were euthanized, lesions removed and homogenised and viable bacteria were counted after dilution and growth on BH1 agar plates (3, 7). Significantly reduced recovery was observed for ST1 (pheP katA) (0.15%) (P<0.003), MJH600 (pheP) (1.9%) (P<0.003) and PC1839 (sarA) (0.04%) (P<0.003). The dashed line shows the limit of recovery. Bar indicates mean value of recovery. Statistical significance was evaluated on the recovery of strains using the Student's t-test with a 5% confidence limit.

FIG. 7. Growth phenotype and complementation of MJH600 (pheP). Strains were incubated overnight in a microaerobic environment on pig serum agar without (A) or with (B) added phenylalanine (1 mM final concentration). Growth of MJH620 (8325-4 pMAL43R) and MJH621 (pheP Pmal43R) on pigserum agar (C). For complementation studies pMAL43 and Pmal43R were electroporated into 8325-4 (wild-type) and MJH600 (pheP). The pheP gene was cloned directly in *S. aureus* due to toxicity of the gene in *E. coli*, which prevented complementation of transport mutants of *E. coli*.

EXAMPLES

Tn917 Library Screen

Figure 4:
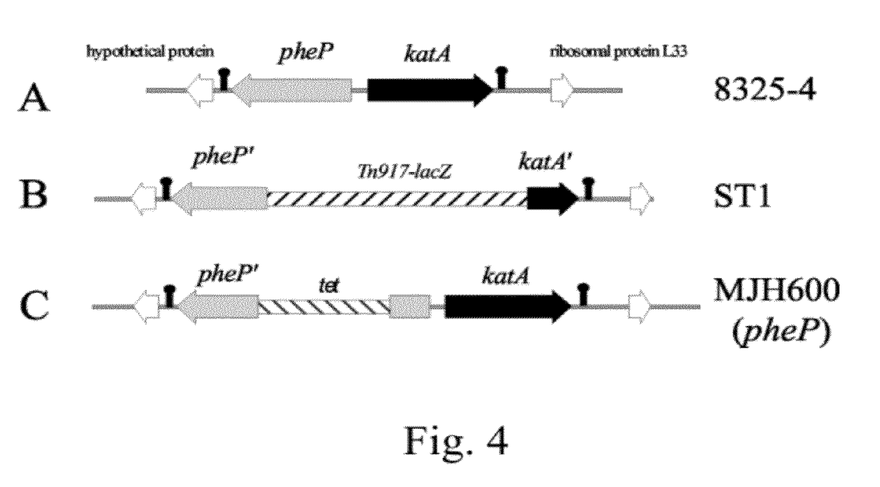

A screen of *S. aureus* Tn917 library transposants with an altered ability to survive carbon starvation identified strain ST1. Sequencing determined that the transposon insertion had produced a large deletion of the katA gene, encoding catalase, and a smaller deletion in the divergently transcribed pheP gene, which encodes a putative amino acid permease (FIGS. 4A, B).

Analysis of PheP Gene

Analysis of the PheP sequence revealed that it has twelve non-contiguous regions of hydrophobicity indicative of membrane-spanning domains. The protein has significant homology with members of the amino acid-polyamine-organocation (APC) superfamily of transport proteins (Jack et al. Microbiology. 146:1797-814 (2000) and Saier, M. H. Microbiology. 146:1775-1795 (2000)). *S. aureus* PheP exhibits greatest sequence identity with *E. coli* LysP (44.6%), which functions as a lysine permease, and *B. subtilis* RocE (34.9%), which functions as an arginine and ornithine permease.

Figure 5:
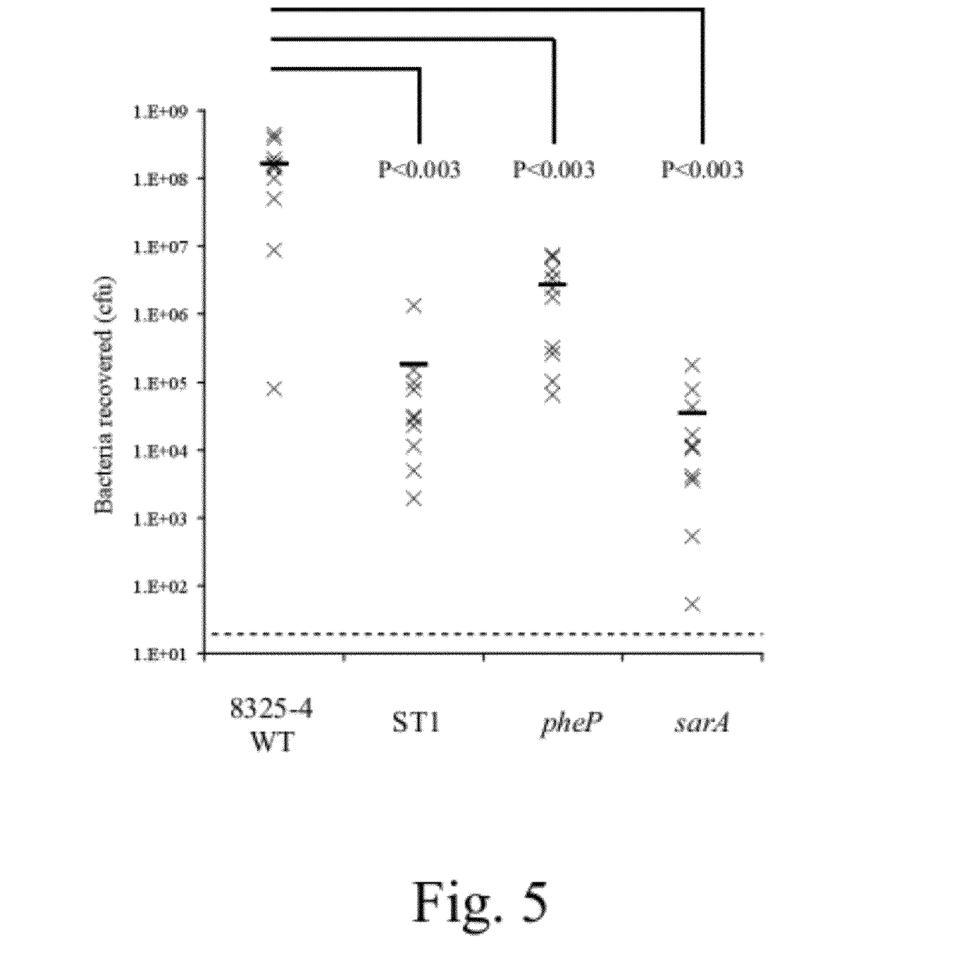

When the virulence of ST1 (pheP katA) was tested in a murine abscess model of infection it had significantly reduced recovery (0.15%) (P<0.003) compared to the isogenic parent strain, 8325-4. The level of recovery for ST1 (pheP katA) was similar to that for the virulence regulator mutant, sarA (0.04%) (P<9,993) (FIG. 5). In contrast the recovery of ST16 (katA), as described previously (Horsburgh, et al. Infect. Immun. 69:3744-3754 (2001)), was not significantly different from that of the 8325-4 (wild-type—suggesting that the reduced virulence of ST1 (pheP katA) was due to inactivation of the pheP gene.

An allelic replacement mutant, MJH600 (pheP) (FIG. 4C) was constructed to determine if inactivation of pheP was the contributing factor for the reduced virulence of ST1. Allelic replacement was achieved by amplifying the pheP gene in upstream and downstream fragments using primers CCAGAATTCTGCCAATGATTAACTCTAATCG (SEQ ID NO: 1) with ATGATGGTACCAGTAGCTACAAATAGACCAGTCC (SEQ ID NO: 2) and AGAGGATCCGCATGTCGCAATCGTATTTGTGACC (SEQ ID NO: 3) with GGACTGGTCTATTTCTAGCTACTGGTACCATCAT (SEQ ID NO: 4). The tetracycline resistance gene (tet) from pDG1513 (Guerot-Fleury, et al. Gene 167:335-336 (1995)) was amplified using primer CCGGTACCCGGATTTTATGACCGATGATGAAG (SEQ ID NO: 5) with CCGGTACCTTAGAAATCCCTTTGAGAATGTTT (SEQ ID NO: 6).

Following purification, the three separate PCR products were digested with BamHI/KpnI, EcoRI/KpnI and KpnI, respectively, and simultaneously ligated to BamHI/EcoRI digested pAZ106 (Kemp et al, J. Bacteriol. 173:4646-4652 (1991), Sambrook et al. One tetracycline resistant clone, Pmal32, was used to transform electrocompetent *S. aureus* RN4220 (Schenk, S, and R. A. Ladagga. Lett. 94:133-138 (1992)) and resolved by outcross via transduction of *S. aureus* 8325-4 using φ11.

PheP Mutant Studies

MJH600 (pheP) had reduced virulence (P<0.003) compared with 8325-4 (wild-type) when tested in a murine abscess model (FIG. 5). This demonstrated that reduced virulence was associated with mutation of pheP and confirmed that the inactivated permease gene was the determinant responsible for the reduced virulence of ST1. The virulence of ST1 (katA pheP) was significantly reduced (P<0.02) relative to that of MJH600 (pheP), suggesting that katA might contribute to survival in a pheP mutant. MJH600 (pheP) showed a similar exoprotein profile to 8325-4 (wild-type) ruling out major effects of the mutation on expression of known extracellular virulence factors (data not shown). Reduced virulence of MJH600 (pheP) was similarly observed in a *Drosophila melonogaster* model of infection (A. Needham and S. J. Foster, unpublished data).

Mutant Complementation Studies

Figure 6:
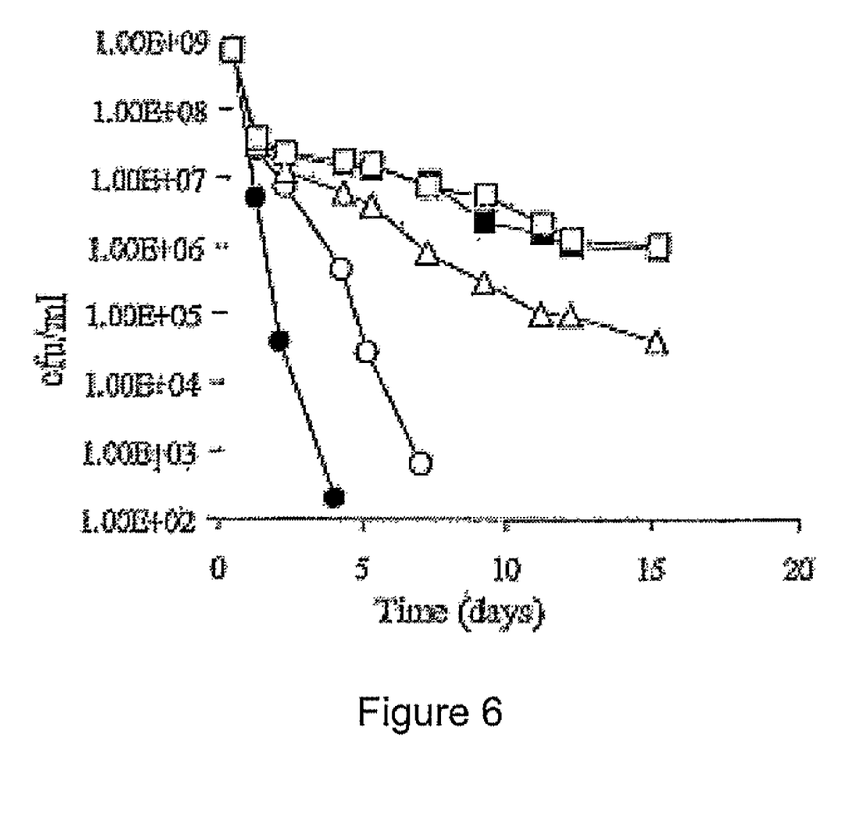
FIG. 6. Starvation survival capabilities of 8325-4 (wild-type) (■), ST1 (●), ST16 (katA) (O) and MJH600 (pheP) (Δ) MJH621 (pheP Pmal43R) (□) after prolonged aerobic incubation in glucose-limiting CDM (22). Samples were aseptically removed at the times indicated and viability was assessed by dilution and counting colonies after 14 h incubation on BHI agar. The experiment was repeated three times giving very similar results; results from a representative experiment are shown.

ST16 (katA) has reduced capacity to survive glucose starvation (Horsburgh et al. Infect. Immun. 69:3744-3754 (2001) and Watson et al, J. Bacteriol. 180:1750-1758 (1998)). Since ST1 (katA pheP) had reduced survival compared to ST16 (katA) during prolonged aerobic incubation in glucose-limiting CDM, the starvation survival of MJH600 (pheP) was tested. MJH600 (pheP) lost viability more rapidly than the parental strain, such that after five days viability was ten times lower than 8325-4 (wild-type) (FIG. 6). Survival was restored by the presence of pMAL43R, containing a full-length copy of the pheP gene on the complementation vector pMK4 (Sullivan et al, Gene 29:21-26 (1984)) (FIG. 6). Plasmid pMAL43R was constructed by PCR amplifying pheP using primer GAGAGGATCCTAGATGGGAGACTAAATATGG (SEQ ID NO: 7) with CACAGAATTCGAATGGTAACATG-GTAATAAT (SEQ ID NO: 8); the product was digested with BamHI/EcoRI, ligated to pMK4 and cloned directly in *S. aureus* RN4220.

Figure 7:
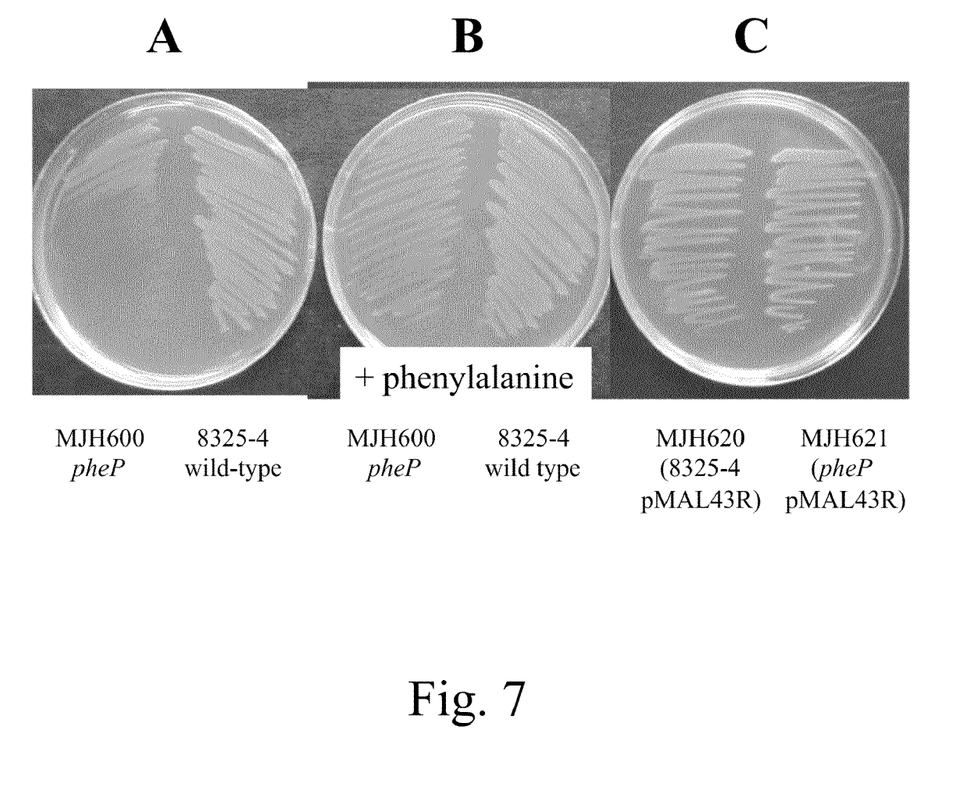

MJH600 (pheP) grew similarly to the present strain, 8325-4 on nutrient and chemically defined medium (CDM) under all conditions tested (data not shown). In contrast, a strong growth defect was observed on pig serum agar (Wiltshire et al, Infect. Immun. 69:5198-5202 (2001)) for MJH600 (pheP) in microaerobic (5% $CO_2$, 87% $N_2$, 8% $O_2$) (FIG. 7A) and anaerobic conditions (data not shown); normal growth was observed for aerobic growth on pig serum agar. Addition of micromolar concentrations of components from CDM identified that phenylalanine completely restored normal growth of MJH600 (pheP) (FIG. 7B), indicating that the permease mutant was likely to have a defect in phenylalanine uptake. The growth defect was also rescued by complementation using Pmal43R indicating that only the pheP mutation was responsible for the observed phenotype (FIG. 7C).

CONCLUSIONS

The ability of *S. aureus* to scavenge amino acids from the host during infection would appear to be an important adaptation to growth in vivo. *S. aureus* 8325-4 is not auxotrophic for phenylalanine (Taylor, D. and K. T. Holland. J. Appl. Bacteriol. 66:319-329 (1989)). Biosynthesis must not be sufficient, however, to fulfil cellular growth requirements in an environment such as the abscess, thereby creating a requirement for phenylalanine uptake during infection.

The invention claimed is:

1. An isolated antigenic polypeptide encoded by an isolated nucleic acid sequence selected from the group consisting of:
   i) SEQ ID NO: 13; and
   ii) a nucleic acid sequence that is degenerate as a result of the genetic code to SEQ ID NO: 13, wherein the polypeptide consists of SEQ ID NO: 14.

2. A medicament comprising the antigenic polypeptide of claim 1.

3. The antigenic polypeptide of claim 1, wherein the polypeptide has phenylalanine permease activity.

4. The medicament of claim 2 wherein the medicament comprises a carrier and/or adjuvant.

5. An isolated antigenic polypeptide consisting of SEQ ID NO: 14.

6. A composition comprising the isolated antigenic polypeptide of claim 5 and at least one component selected from the group consisting of: carriers; and adjuvants.

7. An isolated antigenic polypeptide consisting of 15 consecutive amino acids of SEQ ID NO: 14.

8. A composition comprising the isolated antigenic polypeptide of claim 7 and at least one component selected from the group consisting of: carriers; and adjuvants.

* * * * *